United States Patent
Bloecher et al.

(10) Patent No.: US 9,562,838 B2
(45) Date of Patent: Feb. 7, 2017

(54) MEASURING ELEMENT MADE OF STEEL WITH HARDENED EDGE ZONE

(71) Applicant: WIKA Alexander Wiegand SE & Co. KG, Klingenberg (DE)

(72) Inventors: Rolf Bloecher, Miltenberg (DE); Rolf Kaufmann, Schneeberg (DE); Armin Hawlik, Amorbach (DE)

(73) Assignee: WIKA ALEXANDER WIEGAND SE & CO. KG, Klingenberg (DE)

( * ) Notice: Subject to any disclaimer, the term of this patent is extended or adjusted under 35 U.S.C. 154(b) by 264 days.

(21) Appl. No.: 14/221,167

(22) Filed: Mar. 20, 2014

(65) Prior Publication Data
US 2015/0253230 A1    Sep. 10, 2015

(30) Foreign Application Priority Data
Mar. 10, 2014 (DE) .................. 10 2014 204 348

(51) Int. Cl.
| | |
|---|---|
| *C21D 9/08* | (2006.01) |
| *G01N 3/48* | (2006.01) |
| *G01N 33/20* | (2006.01) |
| *G01L 7/04* | (2006.01) |
| *G01L 7/02* | (2006.01) |
| *G01L 7/00* | (2006.01) |
| *G01L 7/06* | (2006.01) |
| *G01L 19/10* | (2006.01) |

(52) U.S. Cl.
CPC ............... *G01N 3/48* (2013.01); *G01N 33/20* (2013.01); *C21D 9/08* (2013.01); *G01L 7/00* (2013.01); *G01L 7/024* (2013.01); *G01L 7/04* (2013.01); *G01L 7/041* (2013.01); *G01L 7/043* (2013.01); *G01L 7/048* (2013.01); *G01L 7/063* (2013.01); *G01L 19/10* (2013.01)

(58) Field of Classification Search
CPC ............ G01L 7/041; G01L 7/043; G01L 7/00; G01L 7/024; G01L 7/04; G01L 7/048; G01L 7/063; G01L 19/10
USPC .. 73/741, 732, 730, 742, 743, 756; 148/590, 148/206, 519, 592
See application file for complete search history.

(56) References Cited

U.S. PATENT DOCUMENTS

| | | | | |
|---|---|---|---|---|
| 2,883,995 | A | * | 4/1959 | Astley ....................... G01L 7/00 137/82 |
| 3,232,116 | A | * | 2/1966 | Perkins ................... G01L 7/041 73/743 |
| 3,757,582 | A | * | 9/1973 | Sellmaier ................ G01L 7/041 73/741 |
| 3,975,967 | A | * | 8/1976 | Conti ...................... G01L 7/041 73/732 |

(Continued)

OTHER PUBLICATIONS

Fernandes et al. "Wear of plasma nitrided and nitrocarburized AISI 316L austenitic stainless steel". Journal of Achievements in Materials and Manufacturing Engineering 40/2 (2010) 175-179. Accessed online "http://www.journalamme.org/papers_vol40_2/4029.pdf".*

(Continued)

*Primary Examiner* — Lisa Caputo
*Assistant Examiner* — Jonathan Dunlap
(74) *Attorney, Agent, or Firm* — Miles & Stockbridge PC

(57) ABSTRACT

A steel measuring element is provided. The steel measuring element is made of an austenitic chromium-nickel steel with a low carbon and nitrogen content for measuring pressure, with an edge zone being provided with increased hardness.

16 Claims, 3 Drawing Sheets

(56) References Cited

U.S. PATENT DOCUMENTS

| | | | | |
|---|---|---|---|---|
| 4,050,963 | A | * | 9/1977 | Kunioka ................ C21D 9/085 148/510 |
| 4,237,738 | A | * | 12/1980 | Wetterhorn ............ G01L 7/041 73/740 |
| 4,413,525 | A | * | 11/1983 | Conti ...................... G01L 7/041 228/151 |
| 4,615,219 | A | * | 10/1986 | Ache ...................... G01L 7/041 73/741 |
| 4,939,338 | A | * | 7/1990 | Bregy .................... B23K 9/232 219/118 |
| 5,115,676 | A | * | 5/1992 | Lee ........................ G01L 9/0072 361/283.4 |
| 6,085,595 | A | * | 7/2000 | Ferguson ................ G01L 7/024 73/730 |
| 6,552,280 | B1 | * | 4/2003 | Tellenbach ............ G01G 21/26 148/206 |
| 6,578,429 | B1 | * | 6/2003 | Danna .................... G01D 5/04 73/732 |
| 6,887,322 | B2 | * | 5/2005 | Smith ...................... C21D 9/08 148/516 |
| 7,503,222 | B1 | * | 3/2009 | Bessette .................. G01K 1/02 73/740 |
| 2005/0098244 | A1 | * | 5/2005 | Okada ..................... C21D 7/06 148/592 |
| 2007/0113686 | A1 | * | 5/2007 | Desrochers ............ G01N 1/22 73/863.33 |
| 2007/0137734 | A1 | * | 6/2007 | Pawar ................. A61F 2/30767 148/206 |
| 2007/0157997 | A1 | * | 7/2007 | Minemura ............... C23G 5/00 148/206 |
| 2008/0264174 | A1 | * | 10/2008 | Nomura ................ G01L 13/025 73/754 |
| 2009/0235759 | A1 | * | 9/2009 | Bitto .................... G01F 1/8409 73/861.355 |
| 2014/0230824 | A1 | * | 8/2014 | Lucchina .......... A61M 16/0434 128/207.15 |

OTHER PUBLICATIONS

Triwiyanto et al. "The Influence of Nitriding Time of AISI 316L Stainless Steel on Microstructure and Tribological Properties". Asian Journal of Scientific Research, 6: 323-330. Accessed online "http://scialert.net/fulltext/?doi=ajsr.2013.323.330".*

* cited by examiner

MEASURING ELEMENT MADE OF STEEL WITH HARDENED EDGE ZONE

CROSS-REFERENCE TO RELATED APPLICATIONS

This application claims priority to German (DE) Patent Application No. 102014204348.4, filed on Mar. 10, 2014, the disclosure of which is incorporated herein by reference in its entirety.

TECHNICAL FIELD

The invention relates to an elastic measuring element for analyzing pressure or temperature, comprising a sheet or tube which is equipped with a defined strength at a defined depth in an edge area and thus improved with respect to alternating loads in continuous operation.

BACKGROUND

It is known to optimize steel or stainless steel tubes for use with respect to service life and other characteristics, which can change disadvantageously over time and temperature, through autofrettage. It is further known that steel can be hardened, and that, for example, surface and edge layers can be hardened within limits in a targeted manner through a wide variety of methods, such as by influencing the temperature. For this purpose, the material is brought to certain temperatures, for example in furnaces or by means of electrical induction, and then further processed. Moreover, special corrosion-resistant steels or stainless steels are described for special applications which cannot be hardened by the means described above.

The application of additional layers is also known in order to protect steel from certain influences, such as the application of paint in especially corrosive environments. Such problems also arise particularly for tubes in an industrial setting or in measuring elements such as manometers, for example.

SUMMARY

Embodiments of the present invention provide a steel measuring element for continuous use under alternating bending actions, wherein the steel measuring element is made of a non-precipitation-hardenable austenitic chromium-nickel steel, the material edge zone of the steel measuring element is provided with increased strength, the hardness of the material edge zone has a Vickers hardness of at least 500 or 1.5 to 2 times the initial hardness of the basic material, and the material edge zone with increased strength has a thickness of 2 to 50 micrometers.

Embodiments of the present invention also provide a pressure measurement system comprising a pressure port that leads out of a housing and a measuring element that drives an indicator in front of a scale and an elastic tube which is connected in a pressure-tight manner to the pressure port and coupled with the measuring element, wherein the elastic tube is made of an austenitic chromium-nickel steel with a carbon content of up to 0.03% and less than 2% manganese and up to 0.11% nitrogen, the elastic tube has an edge layer of increased strength, the edge layer is introduced into the inside and outside of the tube, the hardness of the edge layer on the tube between the outer edge region is 500 to 1200 Vickers hardness, and the edge layer is introduced into the inside and outside of the tube and has a thickness of at least 5 to 10 μm.

There has thus been outlined, rather broadly, certain embodiments of the invention in order that the detailed description thereof herein may be better understood, and in order that the present contribution to the art may be better appreciated.

Before explaining at least one embodiment of the invention in detail below, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION

Figure 1:
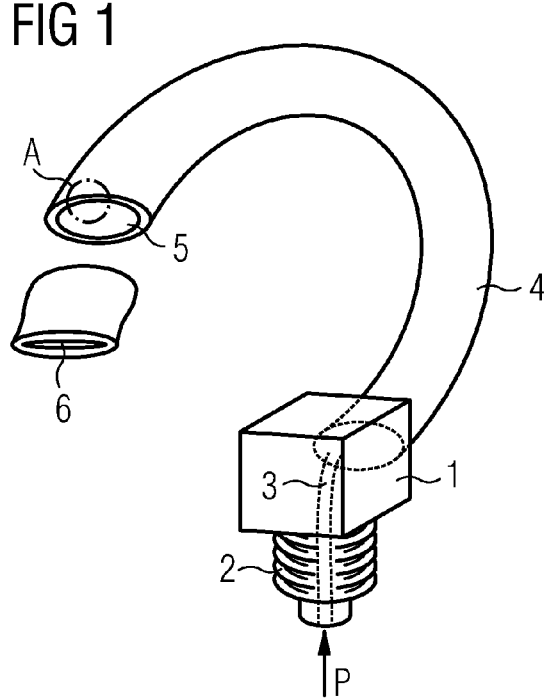
FIG. 1 shows a base body of a manometer, according to an embodiment of the present invention.

The invention will now be described with reference to the drawing figures, in which like reference numerals refer to like parts throughout.

Aspects of the invention provide a cost-effective solution for improving the service life of functional elements, particularly tubes and sheets, made of special types of steel in special applications with respect to continuous elastic use under alternating loads, particularly alternating bending. These aspects are achieved with a construction using a treated special steel such as that described in the independent claims.

Generally, embodiments of the present invention are based on an approach of creating a material construction in which the basic material on the interior should remain as unchanged as possible while, through appropriate treatment, an edge zone is created from the outside which has a greater hardness than the basic material.

The material construction presented here—for example, on a tube—has a modification in which the edge layer of the steel tube is changed in strength and material depth such that the alternating load or bending strength, as well as the fatigue strength, are several times greater in connection with compressive strength than in the starting or basic material.

To do this, the strength of an austenitic chromium-nickel steel, for example in the form of a tube, is preferably altered on the inside and outside such that it has a hardness of 800 to 1200 HV 0.01 (Vickers hardness measured with 0.01 kg test load), which is introduced into an edge region with a layer thickness of 2 to 50 µm, preferably 2-20 µm.

Austenitic chromium-nickel steel (hereinafter also called special steel, stainless steel or steel) from material group 8 according to ISO TR 15608:2013 or from material group 316L according to ASME, which is otherwise not considered to be hardenable, acquires increased strength as a result of this process, which is particularly advantageous if the tube is subjected to an especially large number of bending cycles. This is also especially true of materials 1.4404, 1.4435 and 1.4571, which are particularly regarded as not being precipitation-hardenable. This is particularly due to the low amount of carbon (C) and nitrogen (N) in the basic material.

Non-precipitation-hardenable steel is understood as being a steel that is generally classified as such by the usual standards, including those referenced here. Likewise, these steels could also be subjected to a precipitation process, but little to no measurable changes would be achieved due to the low amounts mentioned above.

However, it has particularly been possible to harden even the abovementioned special steels without the use of conventional precipitation hardening, with these steels being particularly characterized by the following composition of the alloy elements in iron (Fe):
Carbon C: 0-0.03%
Nitrogen N: 0-0.11%
Manganese Mn: 0-2.00%
Molybdenum Mo: 2-3.00%
Chromium Cr: 16-20%
Nickel Ni: 10-15%

The edge layer is produced, for example, through the defined introduction of foreign atoms, preferably carbon and nitrogen, from the outside into the edge layer zone.

Preferably, this is also achieved for alloys with a carbon content of up to 0 to 0.08%.

The edge layer structure can be used particularly advantageously when manufacturing measuring tubes or membranes for pressure measurement devices from the abovementioned material which are also under a pressure load during the alternating loads. Measuring tubes are loaded with alternating pressures, for example, and move back and forth analogously to the pressure load. In particular, such a measuring tube can also be embodied with an elliptical cross section and coupled with a measuring element which drives an indicator.

Here, the requirements are made additionally difficult if the measuring tube is mounted in a manometer at a location with vibration.

In that case, numerous influences converge. For one, deformational forces act on the tube cross section through deformation under internal pressure loading, because the elliptical tube is deformed and approaches a round cross section; for another, fatigue, alternating and pressure loads act on the measuring tube when the internal pressure changes, which are additionally overlaid with vibrations from the application.

However, only stainless steel or special steel can be used in many applications due to their resistance to corrosion. It has turned out that a special steel element exhibits a substantial improvement in creep strength; what is more, the loads for maximum deflection and maximum stress are improved in the edge region. Alternatively, such a layered structure can be provided with hardened membranes of stainless steel or special steel on one or both sides. In this way, the abovementioned advantages can also be achieved in measuring devices with a membrane, for example.

Embodiments of the present invention comprise at least the following points.

Point 1. Steel measuring element for continuous use under alternating bending actions, wherein the steel measuring element is made of a non-precipitation-hardenable austenitic chromium-nickel steel, the material edge zone of the steel measuring element is provided with increased strength, the hardness of the material edge zone has a Vickers hardness of at least 500 or 1.5 to 2 times the initial hardness of the basic material, and wherein the material edge zone with increased strength has a thickness of 2-50 micrometers.

Point 2. Steel measuring element according to point 1, wherein the steel measuring element is tubular, being round, oval or elliptical, or shaped like a membrane.

Point 3. Steel measuring element according to point 1 or 2, wherein the steel contains the following alloy components:
Carbon C: 0-0.03%
Nitrogen N: 0-0.11%
Manganese Mn: 0-2.00%
Molybdenum Mo: 2-3.00%
Chromium Cr: 16-20%
Nickel Ni: 10-15%
Iron Fe: Remainder Point 4. Steel measuring element according to any one of the preceding points, wherein the steel element is provided on the inside and outside, or on both sides, with a material edge zone that has increased strength and increased hardness.

Point 5. Steel measuring element according to point 3 or 4, wherein the carbon C portion of the alloy is 0-0.08%.

Point 6. Steel measuring element according to any one of the preceding points 1 to 4, wherein the tubular steel measuring element is sealed, particularly welded closed, at one end and a measuring element carrier with a pressure port thread is mounted on the other end, or wherein a measuring element that drives an indicator in front of a scale is particularly coupled with the welded-closed end.

Point 7. Steel measuring element according to any one of the preceding points, wherein the steel measuring element can be loaded from one side with ambient pressure and from the other side with a measurement pressure or process pressure via the pressure port.

Point 8. Steel measuring element according to any one of the preceding points, wherein the steel of the steel measuring element is selected from material standard group 316 L according to ASME, or material group 8 according to ISO TR 15608:2013 (austenitic steel), or material group designation 1.4404, 1.4435 or 1.4571.

Point 9. Steel measuring element according to any one of the preceding points, wherein the material edge zone is characterized by a hardness corridor that is bordered toward the top by a straight line (31) sloping from 1500 HV 0.01 at the workpiece surface to 500 HV 0.01 at 50 µm depth and toward the bottom by a straight line (33) sloping from 500 HV 0.01 at the workpiece surface to 200 HV 0.01 at 7 µm depth, and its continuation is bordered by a line (32') remaining constant in depth at 200 HV 0.01.

Point 10. Steel measuring element according to point 9, wherein the material edge zone is characterized by a hardness corridor that is bordered toward the top by a straight line (21) sloping from 1200 HV 0.01 at the workpiece surface to 400 HV 0.01 at 20 μm depth and toward the bottom by a straight line (23) sloping from 600 HV 0.01 at the workpiece surface to 200 HV 0.01 at 10 μm depth, and its continuation is bordered by a line (22') remaining constant in depth at 200 HV 0.01.

Point 11. Steel measuring element according to any one of the preceding points, wherein the hardened material edge zone has on its surface side a compound layer consisting of nitrides, carbides or carbonitrides with a thickness of 2 to 10 μm.

Point 12. Steel measuring element according to any one of the preceding points, wherein the hardened material edge zone is only formed on the side of the steel measuring element that is subjected to elevated pressure in the operating state.

Point 13. Steel measuring element according to any one of the preceding points, wherein the material edge zone has an increased surface hardness of 800-1200 HV 0.01 or is 2 to 20 μm thick.

Point 14. Pressure measurement system consisting of a pressure port that leads out of a housing, a measuring element that drives an indicator in front of a scale, and an elastic tube embodied as a steel measuring element according to any one of claims 1 to 10 which is connected in a pressure-tight manner to the pressure port and coupled with the measuring element.

Point 15. Pressure measurement system consisting of a pressure port that leads out of a housing and a measuring element that drives an indicator in front of a scale and an elastic tube which is connected in a pressure-tight manner to the pressure port and coupled with the measuring element, characterized in that the elastic tube is made of an austenitic chromium-nickel steel with a carbon content of up to 0.03% and less than 2% manganese and up to 0.11% nitrogen, the elastic tube has an edge layer of increased strength, the edge layer is introduced into the inside and outside of the tube, the hardness of the edge layer on the tube between the outer edge region is 500-1200 Vickers hardness, and the edge layer is introduced into the inside and outside of the tube and has a thickness of at least 5-10 μm.

FIG. 1 shows a base body of a manometer consisting of a measuring element carrier 1 that is provided with a pressure port thread 2, according to an embodiment of the present invention. A channel 3 leads through the pressure port thread to the interior of the steel measuring element 4, which is made, for example, of one of the abovementioned special steels and bent in the shape of a circular segment spring, also known as a bourdon tube or Schinz tube, preferably with an elliptical cross section 5, which is welded to the measuring element carrier 1 in a sealing manner with pressure port to the channel 3.

This is tightly sealed off at the free end 6 of the steel measuring element by pinching and welding.

In sectional view, one sees the cross section 5 of the measuring element 4 with material thickness A, which has been delivered and hardened in the form of a steel tube, preferably already with an elliptical cross section, before it is welded to the measuring element carrier 1. Nevertheless, it is also possible to harden measuring elements after welding to a measuring element carrier. If treatment is performed before welding, however, one obtains a measuring tube in which the outer edge layer is modified inside and out, which is to say hardened.

Such a tube is subjected to alternating bending actions, for example, when it is loaded with alternating pressures P relative to the outside pressure. The service life is advantageously several times greater in relation to alternating loads than in normal steel measuring tubes.

Usually, such steel measuring tubes are installed in manometers that have a pressure port that leads out of a protective housing.

A measuring element is then usually accommodated in this housing that drives an indicator in front of a scale.

The elastic measuring tube, which is connected in a pressure-tight manner to the pressure port, then drives the coupled measuring element when a pressure load is present; an increase in pressure can thus be indicated using an indicator on a scale.

Figure 2:
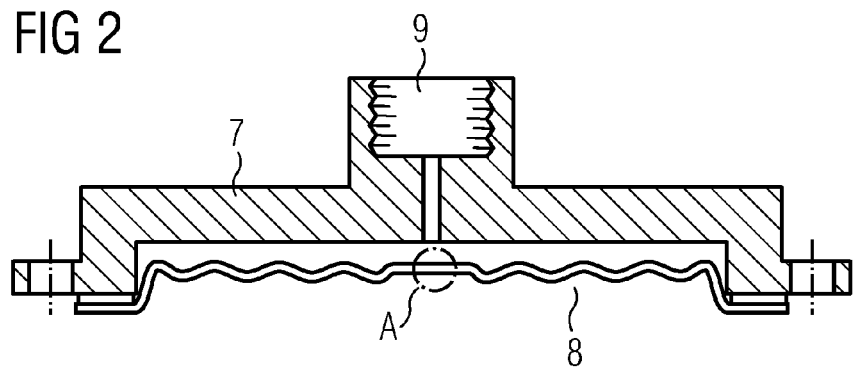
FIG. 2 shows a flange attached to a measuring element, according to an embodiment of the present invention.

FIG. 2 shows a flange 7 that is welded or soldered to a measuring element in the form of a membrane 8, according to an embodiment of the present invention.

Such a flange can be mounted in a pressure-tight manner in front of a measuring element carrier by means of a pressure port 9, for example, in order to prevent penetration into a tube spring 4. For this purpose, the latter is then filled with a pressure transmission fluid, the membrane then transmits pressure fluctuations to the measuring tube spring and is therefore also occasionally subjected to high alternating loads.

The material thickness A of the steel membrane 8 can also advantageously be provided with the edge zone hardening.

Figure 3:
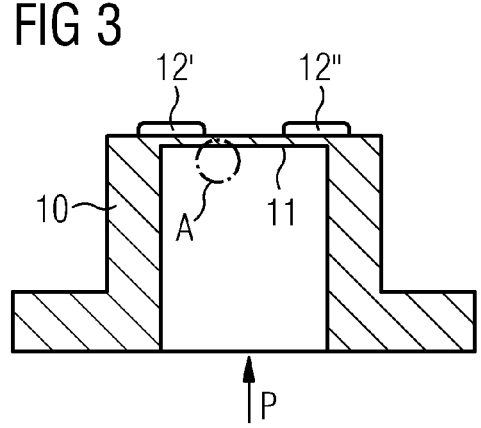
FIG. 3 shows a sensor element, according to an embodiment of the present invention.

FIG. 3 shows a sensor element 10, according to an embodiment of the present invention. An upper molded membrane 11 is provided with elongation resistors 12' and 12" which, when the membrane is loaded with pressure, bring about bending and elongation actions as an ohmic measurement signal and which can be analyzed analogously to the existing pressure P.

Such a steel membrane can also be improved through the hardening process being presented here, particularly in relation to the claimed wall thickness A in relation to alternating loads.

Figure 4:
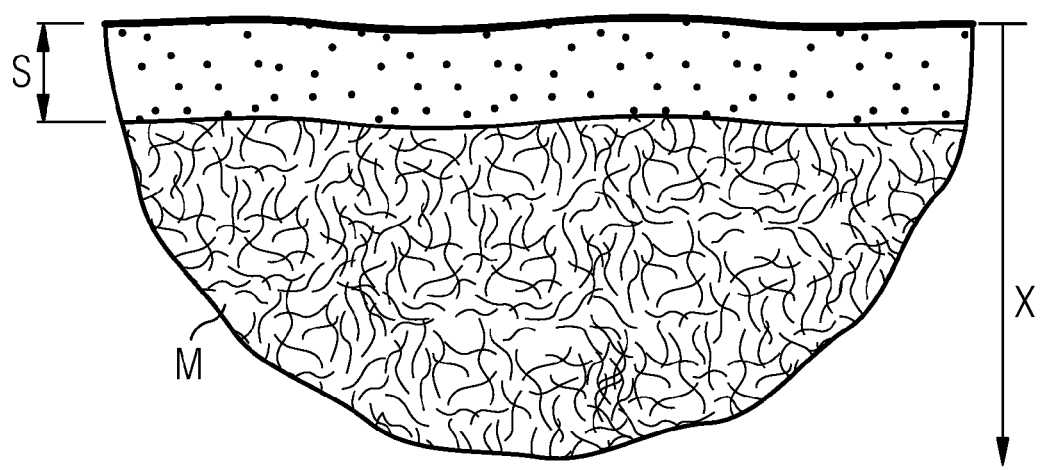
FIG. 4 shows a detailed section A of the material thicknesses of the measuring elements from FIGS. 1, 2 and 3, according to an embodiment of the present invention.

FIG. 4 shows a detailed section A of the material thicknesses of the measuring elements from FIGS. 1, 2 and 3, according to an embodiment of the present invention. The outer edge layer, material edge zone S, is represented here as a component of the basic material M, which has greater strength than the basic material steel M of the tube itself.

The material edge zone S with greater strength has a thickness of 2 to 50 μm, preferably 2 to 20 μm, and has an increasing hardness in the range of 500-1000 to 800-1200 HV 0.01 and thus is 1.5 to 2 times as hard as the basic material.

The hardened zone S of the steel measuring element particularly contains the elements nitrogen and carbon in an increased concentration in this edge zone relative to the basic material.

The hardening of the edge zone can particularly be achieved by enriching the material structure in the edge zone with non-metallic atoms at high temperature or, under temperature, further shifting or amplifying an existing concentration gradient of non-metallic atoms from the outside to the inside in the direction of the basic material M. The introduction can advantageously be achieved using a carbonitration method at relatively low temperatures of 400 to 800° C. in a controlled atmosphere of nitrogen ($N_2$), carbon dioxide ($CO_2$), ammoniac ($NH_3$) and ENDO gas or other $CO$—$H_2$—$CO_2$-mixtures. In this process, the temperature, composition of the atmosphere, and pressure must each be set according to the basic material or intended edge zone hardening.

For example, when using carbon and nitrogen, the process time is accelerated by the simultaneous diffusing-in of carbon and nitrogen. Due to this fact, the carbonization process can take place at lower temperatures (400 to 800° C.) than in a pure carbonization method, for example; furthermore, the thickness of the hardening zone is achieved more quickly. Depending on the basic material, even just 400 to 600° C. is sufficient for this. Depending on the desired hardening and the basic material, the dwell time at the hardening temperature is only 20-25 minutes or several hours, or even up to 24 hours. Through enrichment preferably of nitrogen, the hardening temperature and the critical cooling speed are reduced, so that milder quenching can also be performed. Both factors further reduce the risk of deformation of the tube sections. After the thermal treatment, the workpiece is cooled according to the requirements in water or oil, for example using a ring shower, or air-cooling is also possible.

Figure 5:
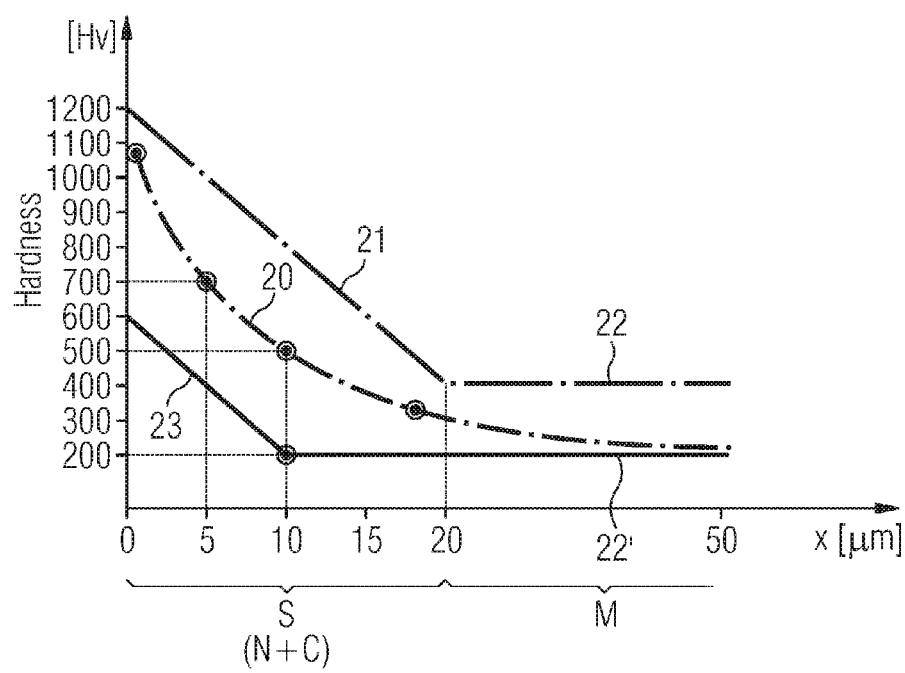
FIG. 5 shows preferred hardness profiles achieved in an improved steel measuring element, according to an embodiment of the present invention.

FIG. 5 shows the preferred hardness profiles achieved in an improved steel measuring element hardened preferably on only one side, according to an embodiment of the present invention.

The curve 20 exhibits an exemplary hardness profile through the material thickness.

By virtue of the formation of a compound zone with a thickness of about 2 μm consisting of nitrides and carbonitrides, hardnesses of over about 1000 HV 0.01 are achieved on the outer edge of the material edge zone S, with the hardness dropping off to 500 HV 0.01 over a width of 2 to 10 micrometers in the underlying diffusion zone, but remaining above the basic hardness of about 300 HV 0.01 of the basic material M.

In particular, however, the hardness of the material edge zone S remains in a region that is bordered in FIG. 5 by lines 21 and 23, 22'. It should be noted here that the lines 22 and 22' represent the upper and lower boundary of the hardness of the basic material. The region of the hardened material edge zone S is therefore characterized by a hardness corridor that is bordered toward the top by the straight line 21 sloping from 1200 HV 0.01 at the workpiece surface to 400 HV 0.01 at 20 μm depth and toward the bottom by the straight line 23 sloping from 600 HV 0.01 at the workpiece surface to 200 HV 0.01 at 10 μm depth, and its continuation is bordered by the line 22' remaining constant in depth at 200 HV 0.01.

Figure 6:
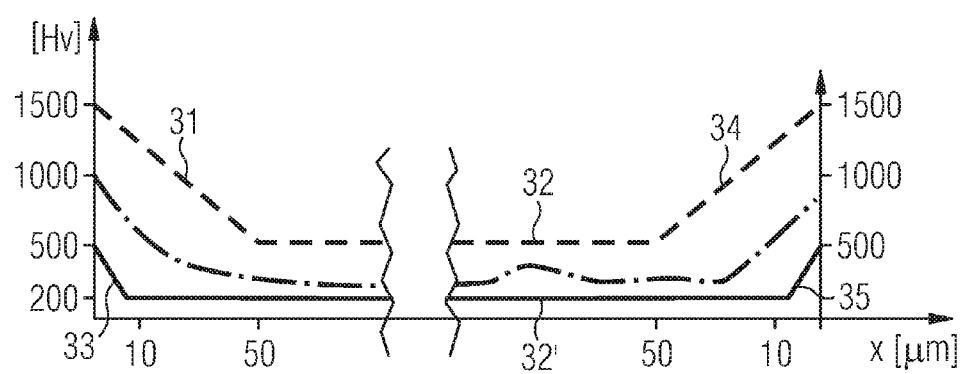
FIG. 6 shows general hardness boundaries, according to an embodiment of the present invention.

FIG. 6 shows somewhat more general hardness boundaries of the inventive hardened material edge zone of a steel measuring element hardened on both sides, in which the advantages of the invention are still ensured. The region of the hardened material edge zone is characterized here by a hardness corridor that is bordered toward the top by the straight line 31 sloping from 1500 HV 0.01 at the workpiece surface to 500 HV 0.01 at 50 μm depth and toward the bottom by the straight line 33 sloping from 500 HV 0.01 at the workpiece surface to 200 HV 0.01 at 7 μm depth, and its continuation is bordered by the line 32' remaining at constant depth at 200 HV 0.01.

The many features and advantages of the invention are apparent from the detailed specification, and, thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and, accordingly, all suitable modifications and equivalents may be resorted to that fall within the scope of the invention.

What is claimed is:

1. A steel measuring element, having a material edge zone, that deforms when subjected to alternating bending actions induced by alternating pressure loads, wherein the steel measuring element is made of a non-precipitation-hardenable austenitic chromium-nickel steel, the material edge zone is provided with increased strength, the hardness of the material edge zone has a Vickers hardness of at least 500 or 1.5 to 2 times the initial hardness of the basic material, and the material edge zone has a thickness of 2 to 50 micrometers, and the steel measuring element is provided on the inside and outside with the material edge zone that has increased strength and increased hardness.

2. The steel measuring element as set forth in claim 1, wherein the steel measuring element is tubular, being round, oval or elliptical.

3. The steel measuring element as set forth in claim 2, wherein the tubular steel measuring element is sealed with a welded closed end, and a measuring element carrier with a pressure port thread is mounted on the other end, and wherein a measuring element that drives an indicator in front of a scale is coupled with the welded-closed end.

4. The steel measuring element as set forth in claim 3, wherein the steel measuring element can be loaded from one side with ambient pressure and from the other side with a measurement pressure or process pressure via the pressure port.

5. The steel measuring element as set forth in claim 1, wherein the non-precipitation-hardenable austenitic chromium-nickel steel contains the following alloy components:
Carbon C: 0 to 0.08%
Nitrogen N: 0 to 0.11%
Manganese Mn: 0 to 2.00%
Molybdenum Mo: 2 to 3.00%
Chromium Cr: 16 to 20%
Nickel Ni: 10 to 15%
Iron Fe: Remainder.

6. The steel measuring element as set forth in claim 5, wherein the carbon C contained in the alloy is 0 to 0.03%.

7. The steel measuring element as set forth in claim 1, wherein the steel of the steel measuring elements is selected from material standard group 316 L according to ASME, or material group 8 according to ISO TR 15608:2013, or material group designation 1.4404, 1.4435 or 1.4571.

8. The steel measuring element as set forth in claim 1, wherein the material edge zone is characterized by a hardness corridor, depicted on a graph of Vickers Hardness versus material edge zone depth, that is bordered toward the top by a straight line sloping from 1500 HV 0.01 at the workpiece surface to 500 HV 0.01 at 50 μm depth and its continuation is bordered by a line remaining constant in depth at 500 HV 0.01, and toward the bottom by a straight line sloping from 500 HV 0.01 at the workpiece surface to 200 HV 0.01 at 7 μm depth and its continuation is bordered by a line remaining constant in depth at 200 HV 0.01.

9. The steel measuring element as set forth in claim 8, wherein the material edge zone is characterized by a hardness corridor, depicted on a graph of Vickers Hardness versus material edge zone depth, that is bordered toward the top by a straight line sloping from 1200 HV 0.01 at the workpiece surface to 400 HV 0.01 at 20 μm depth its continuation is bordered by a line remaining constant in depth at 400 HV 0.01, and toward the bottom by a straight line sloping from 600 HV 0.01 at the workpiece surface to 200 HV 0.01 at 10 μm depth and its continuation is bordered by a line remaining constant in depth at 200 HV 0.01.

10. The steel measuring element as set forth in claim 1, wherein the material edge zone has on its surface side a compound layer consisting of nitrides, carbides or carbonitrides with a thickness of 2 to 10 μm.

11. The steel measuring element as set forth in claim 1, wherein the material edge zone has an increased surface hardness of 800 to 1200 HV 0.01, or is 2 to 20 µm thick.

12. A pressure measurement system, comprising:
a pressure port that leads out of a housing;
a measuring element that drives an indicator in front of a scale; and
an elastic tube embodied as a steel measuring element according to claim 1, which is connected in a pressure-tight manner to the pressure port and coupled with the measuring element.

13. The steel measuring element as set forth in claim 1, wherein the steel measuring element is shaped like a membrane.

14. The steel measuring element as set forth in claim 13, wherein the steel measuring element is provided on both sides with the material edge zone that has increased strength and increased hardness.

15. A steel measuring element, having a material edge zone, that deforms when subjected to alternating bending actions induced by alternating pressure loads, wherein the steel measuring element is made of a non-precipitation-hardenable austenitic chromium-nickel steel, the material edge zone is provided with increased strength, the hardness of the material edge zone has a Vickers hardness of at least 500 or 1.5 to 2 times the initial hardness of the basic material, the material edge zone has a thickness of 2 to 50 micrometers, and the material edge zone is only formed on the side of the steel measuring element that is subjected to elevated pressure in the operating state.

16. A pressure measurement system comprising a pressure port that leads out of a housing and a measuring element that drives an indicator in front of a scale and an elastic tube which is connected in a pressure-tight manner to the pressure port and coupled with the measuring element, wherein the elastic tube deforms when subjected to alternating bending actions induced by alternating pressure loads, the elastic tube is made of an austenitic chromium-nickel steel with a carbon content of up to 0.03% and less than 2% manganese and up to 0.11% nitrogen, the elastic tube has an edge layer of increased strength, the edge layer is introduced into the inside and outside of the tube, the hardness of the edge layer on the tube between the outer edge region is 500 to 1200 Vickers hardness, and the edge layer is introduced into the inside and outside of the tube and has a thickness of at least 5 to 10 µm.

* * * * *